United States Patent
Brewer et al.

(10) Patent No.: US 6,539,255 B1
(45) Date of Patent: Mar. 25, 2003

(54) FULL-TILT EXPONENTIAL DEFIBRILLATION WAVEFORM

(75) Inventors: James E. Brewer, Lino Lakes, MN (US); Patrick J. Tchou, Cleveland, OH (US)

(73) Assignee: Cardiac Science, Inc., Minneapolis, MN (US)

( * ) Notice: Subject to any disclaimer, the term of this patent is extended or adjusted under 35 U.S.C. 154(b) by 0 days.

(21) Appl. No.: 09/354,300

(22) Filed: Jul. 16, 1999

Related U.S. Application Data (60) Provisional application No. 60/093,077, filed on Jul. 16, 1998.

(51) Int. Cl.$^7$ ................................................. A61N 1/39
(52) U.S. Cl. ............................................ 607/5; 607/74
(58) Field of Search ................................ 607/5, 72, 74, 607/7, 8

(56) References Cited

U.S. PATENT DOCUMENTS

| | | | |
|---|---|---|---|
| 3,241,555 A | * | 3/1966 | Caywood et al. ............ 607/5 |
| 3,590,322 A | | 6/1971 | Carr |
| 3,857,398 A | | 12/1974 | Rubin |
| 3,862,636 A | | 1/1975 | Bell et al. |
| 3,886,950 A | | 6/1975 | Ukkestad et al. |
| 4,504,773 A | | 3/1985 | Suzuki et al. |
| 4,610,254 A | | 9/1986 | Morgan et al. |
| 4,619,265 A | | 10/1986 | Morgan et al. |
| 4,637,397 A | | 1/1987 | Jones et al. |
| 4,768,512 A | | 9/1988 | Imran |
| 4,800,883 A | | 1/1989 | Winstrom |
| 4,821,723 A | | 4/1989 | Baker, Jr. et al. |
| 4,823,796 A | | 4/1989 | Benson |
| 4,996,984 A | | 3/1991 | Sweeney |
| 4,998,531 A | | 3/1991 | Bocchi et al. |
| 5,083,562 A | | 1/1992 | de Coriolis et al. |
| 5,097,830 A | | 3/1992 | Eikefjord et al. |
| 5,193,537 A | | 3/1993 | Freeeman |
| 5,205,284 A | | 4/1993 | Freeman |

(List continued on next page.)

FOREIGN PATENT DOCUMENTS

| | | |
|---|---|---|
| GB | 2 280 377 A | 2/1995 |
| WO | WO 93/01861 | 2/1993 |
| WO | WO 95/05215 | 2/1995 |
| WO | WO 95/09673 | 4/1995 |
| WO | WO 95/32020 | 11/1995 |

OTHER PUBLICATIONS

"Defibrillation of the Heart", W.A. Tacker, Jr., Chapter 10, pp. 196–222, 1994.

"On The Intensity–Time Relations for Stimulation By Electric Currents. II", H.A. Blair, The Journal of General Physiology, Rockefeller Institute for Medical Research, vol. 15, pp. 731–755, 1932.

"Optimal Truncation of Defibrillation Pulses," Werner Irnich, Pacing and Clinical Electrophysiology, Futura Publishing Co., vol. 18, No. 4, pp. 673–688, Apr. 1995.

(List continued on next page.)

*Primary Examiner*—George R. Evanisko
(74) *Attorney, Agent, or Firm*—Patterson, Thuente, Skaar & Christensen, P.A.

(57) ABSTRACT

The characteristics of a full-tilt exponential waveform are developed through use of a charge burping model or through use of a transthoracic cell response model. These characteristics are implemented within a pulse delivery circuit, which itself is implemented within an internal defibrillator or within an external defibrillator. The pulse delivery circuit includes at least one switch which starts and stops the delivery of the defibrillation pulse. Delivery of the defibrillation pulse is started by the switch when there is sufficient stored energy to deliver a desired pulse. Delivery of the defibrillation pulse is stopped by the switch when the current flowing through the switch is substantially zero and the exponential waveform of the pulse is substantially fully decayed.

12 Claims, 7 Drawing Sheets

U.S. PATENT DOCUMENTS

| | | | |
|---|---|---|---|
| 5,215,081 A | | 6/1993 | Ostroff |
| 5,275,157 A | | 1/1994 | Morgan et al. |
| 5,282,843 A | | 2/1994 | Freeman |
| 5,350,403 A | * | 9/1994 | Stroetmann et al. ........... 607/5 |
| 5,352,239 A | | 10/1994 | Pless |
| 5,372,606 A | | 12/1994 | Lang et al. |
| 5,385,575 A | | 1/1995 | Adams |
| 5,391,186 A | | 2/1995 | Kroll et al. |
| 5,405,361 A | | 4/1995 | Persson |
| 5,411,525 A | | 5/1995 | Swanson et al. |
| 5,411,526 A | | 5/1995 | Kroll et al. |
| 5,431,686 A | | 7/1995 | Kroll et al. |
| 5,431,688 A | | 7/1995 | Freeman |
| 5,468,254 A | | 11/1995 | Hahn et al. |
| 5,507,778 A | | 4/1996 | Freeman |
| 5,534,015 A | | 7/1996 | Kroll et al. |
| 5,540,721 A | * | 7/1996 | Kroll ........................... 607/75 |
| 5,540,723 A | | 7/1996 | Ideker et al. |
| 5,591,209 A | | 1/1997 | Kroll et al. |
| 5,593,427 A | | 1/1997 | Gliner et al. |
| 5,601,612 A | | 2/1997 | Gliner et al. |
| 5,607,454 A | | 3/1997 | Cameron et al. |
| 5,735,879 A | | 4/1998 | Gliner et al. |
| 5,749,904 A | | 5/1998 | Gliner et al. |
| 5,749,905 A | | 5/1998 | Gliner et al. |
| 5,833,712 A | * | 11/1998 | Kroll et al. ..................... 607/5 |
| 5,991,658 A | * | 11/1999 | Brewer et al. .................. 607/7 |

OTHER PUBLICATIONS

"Choosing the Optimal Monophasic and Biphasic Waveforms for Ventricular Defibrillation," G.P. Walcott, R. G. Walker, A. W. Cates, W. Krassowska, W. M. Smith, R. E. Ideker, Journal of Cardiovascular Electrophysiology, Futura Publishing Co., vol. 6, No. 9, pp. 737–750, Sep. 1995.

"Optimizing Defibrillation Through Improved Waveforms," Michael Block and Günter Breithardt, Pacing and Clinical Electrophysiology, Futura Publishing Co., vol. 18, No. 3, Part II, pp. 526–538, Mar. 1995.

"A Conceptual Basis for Defibrillation Waveforms," Brian G. Cleland, Pacing and Clinical Electrophysiology, Future Publishing Co., vol. 19, No. 8, pp. 1186–1195, Aug. 1996.

"A Minimal Model of the Single Capacitor Biphasic Defibrillation Waveform," Mark W. Kroll, Pacing and Clinical Electrophysiology, Future Publishing Co., vol. 17, No. 11, Part I, pp. 1782–1792, Nov. 1994.

"On The Intensity–Time Relations For Stimulation By Electric Currents. I," H.A. Blair, The Journal of General Physiology, Rockefeller Institute for Medical Research, vol. 15, pp. 709–729, 1932.

"Ventricular Defibrillation Using Biphasic Waveforms: The Importance of Phasic Duration," A.S.L. Tang, S. Yabe, J. M. Wharton, M. Doker, W.M. Smith, R. E. Ideker, Journal of the American College of Cardiology, American College of Cardiology, vol. 13, No. 1, pp. 207–214, Jan. 1989.

A Minimal Model of the Monophasic Defibrillation Pulse, Mark W. Kroll, Pacing and Clinical Electrophysiology, Futura Publishing Co., vol. 16, No. 4, Part I, pp. 769–777, Apr. 1993.

"Low Voltage Shocks Have a Significantly Higher Tilt of the Internal Electric Field Than Do High Voltage Shocks," by James E. Brewer et al., Pacing and Clinical Electrophysiology, vol. 18, No. 1, Part II, pp. 214–220, Jan. 1995.

Strength–Duration and Probability of Success Curves for Defibrillation With Biphasic Waveforms, S.A. Feeser, A.S.L. Tang, K.M. Kavanagh, D.L. Rollins, W.M. Smith, P.D. Wolf, R.E. Ideker, Circulation, American Heart Association, vol. 82, No. 6, pp. 2128–2141, Dec. 1990.

"Improved Defibrillation Thresholds With Large Contoured Epicardial Electrodes and Biphasic Waveforms," E.G. Dixon, A.S.L. Tang, P.D. Wolf, J.T. Meador, M.J. Fine, R.V. Calfee, R.E. Ideker, Circulation, American Heart Association, vol. 76, No. 5, pp. 1176–1184, Nov. 1987.

"Truncated Biphasic Pulses for Transthoracic Defibrillation," G.H. Bardy, B.E. Gliner, P.J. Kudenchuk, J.E. Poole, G.L. Dolack, G. K. Jones, J. Anderson, C. Troutman, G. Johnson, Circulation, American Heart Association, vol. 91, No. 6, pp. 1768–1774, Mar. 1995.

"Transthoracic Defibrillation of Swing With Monophasic and Biphase Waveforms," B.E. Gliner, T.E. Lyster, S.M. Dillion, G.H. Bardy, Circulation, American Heart Association, vol. 92, No. 6, pp. 1634–1643, Sep. 1995.

"Multicenter Comparison of Truncated Biphasic Shocks and Standard Damped Sine Wave Monophasic Shocks for Transthoracic Ventricular Defibrillation," G.H. Bardy, F.E. Marchlinski, A.D. Sharma, S.J. Worley, R.M. Luceri, R. Yee, B.D. Halperin, C.L. Fellows, T.S. Ahern, D.A. Chilson, D.L. Packer, D.J. Wilber, T.A. Mattioni, R. Reddy, R.A. Kronmal, R. Lazzara, Circulation, American Heart Associate, vol. 94, No. 10, pp. 2507–2514, Nov. 1996.

"Mechanisms for Electrical Stimulation of Excitable Tissue," by B.J. Roth, Critical Reviews In Biomedical Engineering, vol. 22, Issues 3 & 4, pp. 253–305, 1994.

"Virtual Electrodes in Cardiac Tissue: A Common Mechanism for Anodal and Cathodal Stimulation," John P. Wikswo, Jr., Shien–Fong Lin, Rashida A. Abbas, Biophysics Journal, vol. 69, No. 6, pp. 2195–2210, Dec. 1995.

"A Mathematical Model of Make and Break Electrical Stimulation of Cardiac Tissue by a Unipolar Anode or Cathode," Bradley J. Roth, Biomedical Engineering, vol. 42, No. 12, pp. 1174–1184, Dec. 1995.

"The Effect of Externally Applied Electrical Fields on Myocardial Tissue," Bradley J. Roth and John P. Wikswo, Jr., Proceedings of the IEEE, vol. 84, No. 3, pp. 379–391, Mar. 1996.

* cited by examiner

FULL-TILT EXPONENTIAL DEFIBRILLATION WAVEFORM

REFERENCE TO RELATED APPLICATION

This application claims the benefit of U.S. Provisional Application No. 60/093,077, filed Jul. 16, 1998, entitled FULL-TILT EXPONENTIAL DEFIBRILLATION WAVEFORM, incorporated herein in its entirety by reference.

FIELD OF THE INVENTION

The present invention relates to internal and external defibrillation pulses and, more particularly, to exponentially decaying defibrillation pulse waveforms that do not utilize truncation.

BACKGROUND OF THE INVENTION

Devices for defibrillating the heart have been known for some time now. Implantable defibrillators are well accepted by the medical community as effective tools to combat ventricular fibrillation for an identified segment of the population. A substantial amount of research in fibrillation and the therapy of defibrillation has been done. Much of the most recent research has concentrated on understanding the effects that a defibrillation shock pulse has on fibrillation and the ability to terminate such a condition.

In general, defibrillation shock pulses are delivered through use of a monophasic waveform or, alternatively, a biphasic waveform. A monophasic waveform is typically a single phase, capacitive-discharge, time-truncated, waveform with exponential decay. A biphasic waveform is defined to comprise two monophasic waveforms that are separated by time and that are of opposite polarity. The first phase is designated $\Phi_1$ and the second phase is designated $\Phi_2$. The delivery of $\Phi_1$ is completed before the delivery of $\Phi_2$ is begun.

After extensive testing, it has been determined that biphasic waveforms are more efficacious than monophasic waveforms. There is a wide debate regarding the exact reasons for the increased efficacy of biphasic waveforms over that of monophasic waveforms. One hypothesis holds that $\Phi_1$ defibrillates the heart and $\Phi_2$ performs a stabilizing action that keeps the heart from refibrillating.

Biphasic defibrillation waveforms are now the standard of care in clinical user for defibrillation with implantable cardioverter-defibrillators (ICDs), due to the superior performance demonstrated over that of comparable monophasic waveforms. To better understand these significantly different outcomes, ICD research has developed cardiac cell response models. Waveform design criteria have been derived from these models and have been applied to monophasic and biphasic waveforms to optimize their parameters. These model-based design criteria have produced significant improvements over previously used waveforms.

In a two paper set, Blair developed a model for the optimal design of a monophasic waveform when used for general bodily electrical stimulation. (1) Blair, H. A., "On the Intensity-time Relations for Stimulation by Electric Currents." I.J. Gen. Physio. 1932; 15:709–729. (2) Blair, H. A., "On the Intensity-time Relations for Stimulation by Electric Currents II." I.J. Gen. Physiol. 1932; 15:731–755. Blair proposed and demonstrated that the optimal duration of a monophasic waveform is equal to the point in time at which the cell response to the stimulus is maximal. Duplicating Blair's model, Walcott extended Blair's analysis to defibrillation, where they obtained supporting experimental results. Walcott, et al., "Choosing the Optimal Monophasic and Biphasic waveforms for Ventricular Defibrillation." J.Cardiovasc. Electrophysio. 1995; 6:737–750.

Independently, Kroll developed a biphasic model for the optimal design of $\Phi_2$ for a biphasic defibrillation waveform as applied internally. Kroll, M. W., "A Minimal Model of the Single Capacitor Biphasic Defibrillation Waveform." PACE 1994; 17:1782–1792. Kroll proposed that the $\Phi_2$ stabilizing action removed the charge deposited by $\Phi_1$ from those cells not stimulated by $\Phi_1$. This has come to be known as "charge burping." Kroll supported his hypothesis with retrospective analysis of studies by Dixon, et al., Tang, et al., and Freese, et al., regarding single capacitor, biphasic waveform studies. See, Dixon, et al., "Improved Defibrillation Thresholds with Large Contoured Epicardial Electrodes and Biphasic Waveforms." Circulation 1987; 76:1176–1184; Tang et al., "Ventricular Defibrillation Using Biphasic Waveforms: The Importance of Phasic Duration." J. Am. Coll. Cardio. 1989; 13:207–214; and Freese, S. A. et al., "Strength Duration and Probability of Success Curves for Defibrillation with Biphasic Waveforms." Circulation 1990; 82:2128–2141. Again, the Walcott group retrospectively evaluated their extension of Blair's model to $\Phi_2$ using the Tange and Freese data sets. Their finding further supported Kroll's hypothesis regarding biphasic defibrillation waveforms as applied to internal defibrillation. For further discussions on the development of the models, reference may be made to PCT publications WO 95/32020 and WO 95/09673 and to U.S. Pat. No. 5,431,686. U.S. Pat. No. 5,431,686 is hereby incorporated by reference.

The "charge burping" hypothesis may be used to develop equations that describe the time course of a cell's membrane potential during a biphasic shock pulse. At the end of $\Phi_1$, those cells that were not stimulated by $\Phi_1$ have a residual charge due to the action of $\Phi_1$, on the cell. The "charge burping" model hypothesizes that an optimal duration for $\Phi_2$ is that duration which removes as much of the $\Phi_1$ residual charge from the cell as possible. Ideally, these unstimulated cells are set back to "relative ground." The "charge burping" model proposed by Kroll is based on the circuit model shown in FIG. 1B, which is adapted from the general model of a defibrillator in FIG. 1A. in FIG. 1B, $R_H$ represents the resistance of the heart, the pair $C_M$ and $R_M$ represent membrane series capacitance and resistance of a single cell. $C_1$ represents the $\Phi_1$ and $\Phi_2$ capacitor set. The node $V_S$ represents the voltage between the internal electrodes, while $V_M$ denotes the voltage across the cell membrane.

It should be noted that the "charge burping" model may also account for removing residual cell membrane potential at the end of a $\Phi_1$ that is independent of a $\Phi_2$ pulse, i.e., $\Phi_2$ is delivered by a set of capacitors separate from the set of capacitors used to deliver $\Phi_1$. This "charge burping" model is constructed by adding a second set of capacitors, as illustrated in FIG. 2. In this figure, in addition to those elements described with reference to FIG. 1B, $C_2$ represents the $\Phi_2$ capacitor set that is separate from $C_1$.

Contrary to the internal defibrillators/defibrillator circuit models described above, external defibrillators can not deliver electrical shock pulses directly to the heart. Rather, external defibrillators must send electrical pulses to the patient's heart through electrodes that are applied to the patient's torso. External defibrillators are useful in any situation where there may be an unanticipated need to provide electrotherapy to a patient on short notice. The advantage of external defibrillators is that they may be used on a patient as needed, then subsequently moved to be used on another patient.

While the moveability of the external defibrillator is indeed a useful advantage, that moveability presents at least two problems not found with internal defibrillators. First, the transthoracic defibrillation problem which results, as explained earlier, from the fact that the external electrodes traditionally deliver their electrotherapeutic pulses to the patients heart by first passing through the patient's chest. Second, the patient variability problem which results from the fact that external electrodes and defibrillators must be able to be used on patient's having a variety of physiological differences. To accommodate that variety, external defibrillators have traditionally operated according to pulse amplitude and duration parameters.

The internal defibrillator models described above, do not fully address the transthoracic defibrillation problem or the patient variability problem. In fact, these two limitations to external defibrillators are not fully appreciated by those in the art. For example, prior art disclosures of the use of truncated exponential monophasic or biphasic shock pulses in implantable or internal defibrillators have provided little guidance for the design of an external defibrillator that will successfully defibrillate across a large, heterogeneous population of patients. In particular, an implantable defibrillator and an external defibrillator can deliver a shock pulse of similar form, and yet, the actual implementation of the waveform delivery system is radically different.

In the past five years, new research in ICD therapy has developed and demonstrated defibrillation models and their associated design rules. These models and rules for the development of defibrillation waveforms and their characteristics were first developed by Kroll and Irnich for monophasic waveforms using effective and rheobase concepts. (1) Kroll, M. W., "A Minimal Model of the Monophasic Defibrillation Pulse." PACE 1993; 15:769. (2) Irnich, W., "Optimal Truncation of Defibrillation Pulses." PACE 1995; 18:673. Subsequently, Kroll, Walcott, Cleland, and others developed the passive cardiac cell membrane response model for monophasic and biphasic waveforms, herein called the cell response model. (1) Kroll, M. W., "A Minimal Model of the Single Capacitor Biphasic Waveform." PACE 1994: 17:1782. (2) Walcott, G. P., Walker, R. G., Cates, A. W., Krassowska, W., Smith, W. M., Ideker, R. E., "Choosing the Optimal Monophasic and Biphasic Waveforms for Ventricular Defibrillation." J. Cardiovasc. Electrophysio. 1995; 6:737. (3) Cleland, B. G., "A Conceptual Basis for Defibrillation Waveforms." PACE 1996; 19:1186.

A significant increase in the understanding of waveform design has occurred and substantial improvements have been made by using these newly developed design principles. Block et al., has recently written a comprehensive survey of the new principles-based theories and their impact on optimizing internal defibrillation through improved waveforms. Block, M., Breithardt, G., "Optimizing Defibrillation through Improved Waveforms." PACE 1995; 18:526.

However, there have not been significant developments in external defibrillation waveforms beyond the two basic monophasic waveforms, i.e., the damped sine or the truncated exponential. To date, their design for transthoracic defibrillation has been based almost entirely on empirically derived data with little to no influence by the important developments in ICD research.

Recently, there has been reported research on the development and validation of a biphasic truncated exponential waveform in which it was compared clinically to a damped sine waveform. For additional background, reference may be made to U.S. Pat. Nos. 5,593,427, 5,601,612, and 5,607, 454. See also, Cliner, B. E., Lyster, T. E., Dillon, S. M., Bard, G. H., "Transthoracic Defibrillation of Swine with Monophasic and Biphasic Waveforms." Circulation 1995: 92:1634–1643; Bardy, G. H., Gliner, B. E., Kudenchuck, P. J. Poole, J. E., Dolack, C. L. Jones, G. K., Anderson J. Troutman, C., Johnson, G., "Truncated Biphasic Pulses for Transthoracic Defibrillation." Circulation 1995; 91:1768–1774; and Bardy, G. H. et al., "For the Transthoracic Investigators: Multicenter Comparison of Truncated Biphasic Shocks and Standard Damped Sine Wave Monophasic Shocks for Transthoracic Ventricular Defibrillation." Circulation 1996: 94: 2507–2514. Although research determined a usable biphasic waveform, there was no new theoretical understanding determined for external waveform design. As such, external waveform design is progressing much like that established in the early stages of theoretical ICD research. The limitations of this determined biphasic waveform are likely due, at least in part, to a lack of principles-based design rules to determine waveform characteristics.

Further, the delivery of a biphasic truncated exponential waveform requires additional consideration of the design of circuit components. Generally, a circuit that delivers a truncated exponential waveform uses switching mechanisms or relays to cut off, or truncate, the waveform. These switching mechanisms truncate the waveform during the time that the defibrillation pulse is being delivered and at a time when there is still a great amount of current flowing through the switching mechanism. Because of the great current, the switching mechanisms are subjected to extreme wear and are prone to failure. Attempting to respond to these failures, U.S. Pat. No. 5,748,427 discloses a method and system for detecting switching mechanism failure in external defibrillators. Alternatively, multiple switching devices may be incorporated into a circuit to avoid failure, U.S. Pat. No. 5,405,361 discloses a multiple switching external defibrillator. Whether introducing special design considerations in the form of failure detection or multiple switches, additional time, money and effort are expended.

In view of the above, there is a need in the art for the development of a transthoracic cell response model and design rules which can be used to develop the characteristics of external defibrillation waveforms. Further, there is a need in the art for an optimally designed waveform which requires minimal truncation, specifically a full-tilt exponential waveform which is defined as an exponential waveform truncated at approximately 95% of the full waveform; at 95% truncation approximately 99.75% of the energy of the defibrillation pulse has been delivered. Moreover, there is a need in the art for internal and an external devices which can deliver this waveform.

SUMMARY OF THE INVENTION

The needs described above are in large measure met by a full-tilt exponential defibrillation pulse waveform of the present invention. The characteristics of the full-tilt exponential waveform are developed through use of a charge burping model or through use of a transthoracic cell response model. These characteristics are implemented within a pulse delivery circuit, which itself is implemented within an internal defibrillator or within an external defibrillator. The pulse delivery circuit includes at least one switch which starts and stops the delivery of the defibrillation pulse. Delivery of the defibrillation pulse is started by the switch when there is sufficient stored energy to deliver a desired pulse. Delivery of the defibrillation pulse is stopped by the switch when the current flowing through the switch is substantially zero and the exponential waveform of the pulse is substantially fully decayed.

DESCRIPTION OF THE PREFERRED EMBODIMENTS

The characteristics of a full-tilt exponential waveform are designed by using the charge burping model of the prior art (internal defibrillation) or by using a transthoracic cell response model (external defibrillation) as described herein. The characteristics of the full-tilt exponential waveform are then implemented within a pulse delivery circuit as described herein. That pulse delivery circuit is then preferably implemented within an internal or external defibrillator, a basic description of each of which is described herein.

Full-Tilt Exponential Waveform Design

The characteristics of a full-tilt exponential waveform for internal defibrillation are preferably developed through the use of the charge burping model, as referenced in the "Background of the Invention" above, and its associated design criteria. The characteristic of a full-tilt exponential waveform for external defibrillation are preferably developed through the use a transthoracic cell response model 10 as depicted in FIG. 3.

Transthoracic defibrillation is generally performed by placing electrodes on the apex and anterior positions of the chest wall. With this electrode arrangement, the main series pathway for current is to pass through the chest wall, the lungs, and on to the heart. Additionally, there are two shunting pathways in parallel with the current pathway to the heart. The first shunting, parallel pathway is created by the lungs shunting current around the heart and the second is created by the thoracic cage. However, it should be noted that the resistivity of the thoracic cage (and the skeletal muscle structure) is low compared to the resistance provided by the lungs. Thus, the high resistivity of the lungs and the resistivity of the shunting pathways are characteristic elements of external defibrillation which help to distinguish external defibrillation from internal, e.g., intracardiac and implantable, defibrillation.

Figure 1A:
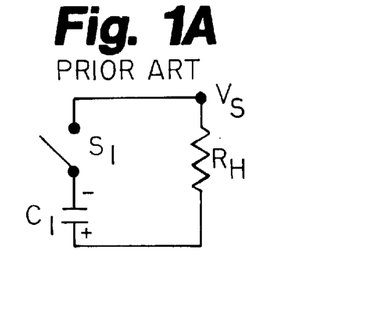
FIG. 1A depicts a prior art, general circuit model of an internal defibrillator.
Figure 1B:
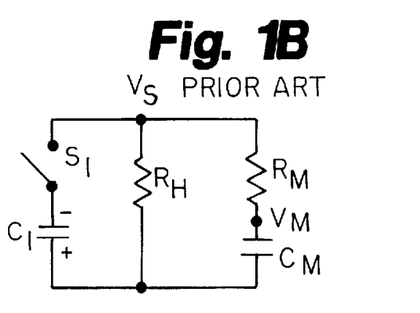
FIG. 1B depicts a prior art expanded circuit model of an internal defibrillator.
Figure 2:
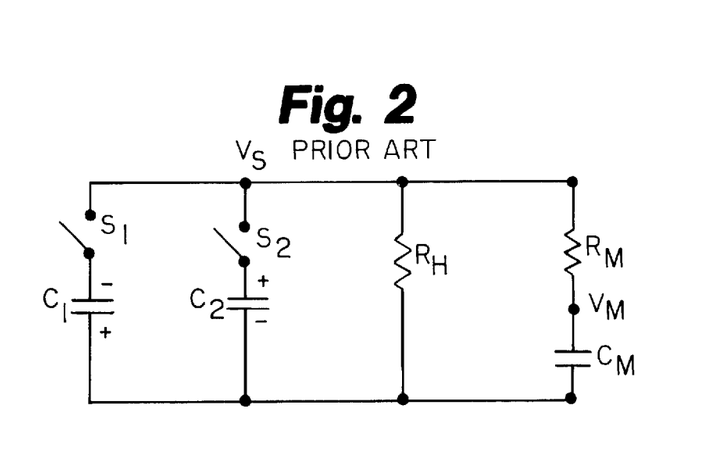
FIG. 2 depicts a prior art expanded circuit model of an internal defibrillator including two capacitor sets.

These characteristic elements are reflected in transthoracic cell response model 10, which is an expansion of the original "charge burping" model of FIGS. 1A, 1B and 2. As such, transthoracic cell response model 10 includes the following elements: (1) $R_S$ which represents the resistance of the defibrillation system, including the resistance of the electrodes; (2) $R_{CW}$ and $R_{LS}$ which represent the resistance of the chest wall and lungs, respectively, in series with the resistance of the heart, $R_H$; (3) $R_{TC}$ and $R_{LP}$ which represent the resistance of the thoracic cage and the lungs, respectively, in parallel with the resistance of the heart, $R_H$; and, (4) the elements from the original "charge burping" model, including $R_M$ which represents the resistance of a single cell membrane in series with $C_M$ which represents the capacitance of the cell membrane. Capacitors $C_1$ and $C_2$ are the charging capacitor sets for the delivery of a first waveform of a biphasic waveform, $\Phi_1$, and for the delivery of a second waveform of a biphasic waveform, $\Phi_2$, respectively.

Figure 3:
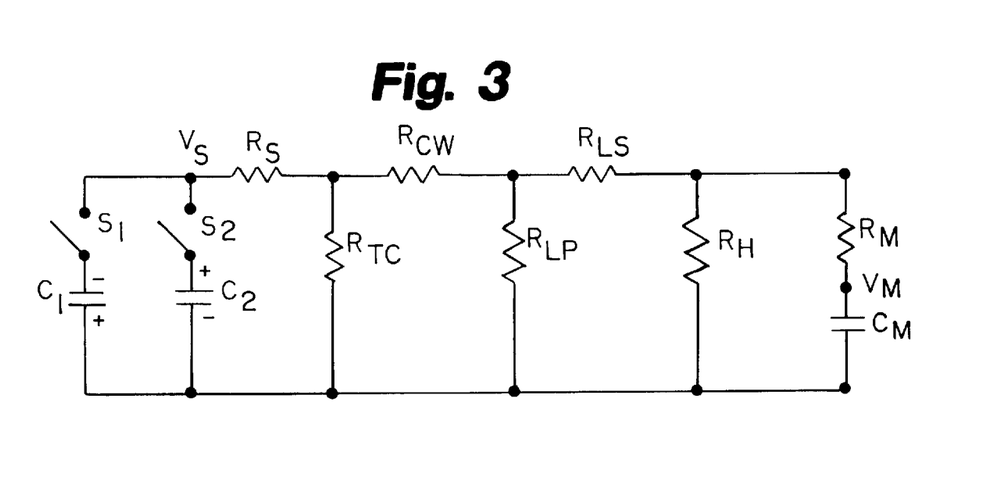
FIG. 3 depicts a transthoracic cell response circuit model.
Figure 4A:
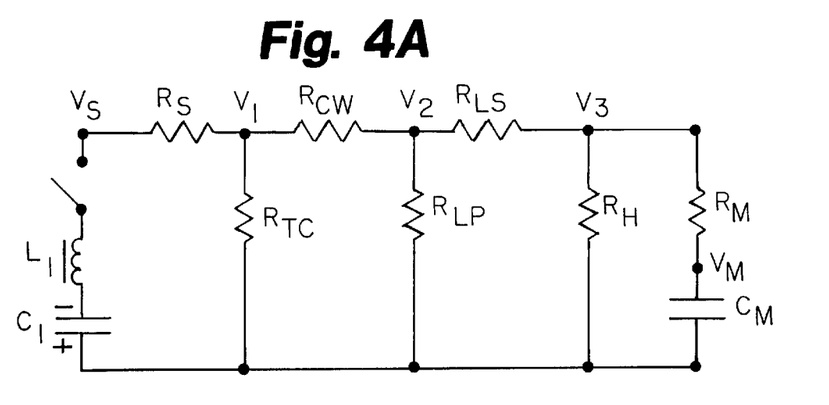
FIG. 4A depicts an alternative embodiment of the transthoracic cell response circuit model of FIG. 3.
Figure 4B:
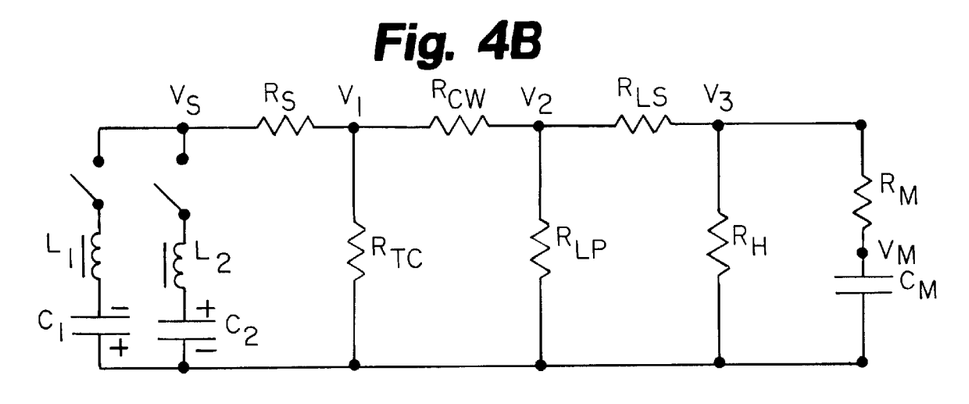
FIG. 4B depicts another alternative embodiment of the transthoracic cell response circuit model of FIG. 3.

FIGS. 4A and 4B depict alternative embodiments of transthoracic cell response model 10 of FIG. 3. Here, each circuit additionally incorporates an inductor in series with each charging capacitor, e.g., $L_1$ in series with $C_1$ in FIG. 4A and $L_1$ in series with $C_1$ and $L_2$ in series with $C_2$ in FIG. 4B. The inductors act to produce a shock pulse that is in the form of a damped sine wave. Note that FIG. 4A represents a monophasic external defibrillator while FIG. 4B represents a biphasic external defibrillator.

Based on transthoracic cell response model 10 of FIG. 3, monophasic/biphasic waveform design rules may be developed. First, the transchest transfer function must be determined. The transchest transfer function is defined as the voltage that is applied across each myocardial cell during an external defibrillation shock and is indicated on transthoracic cell response model 10 as $V_3$. Using nodal analysis, $V_3$ is determined as follows.

Node 1:

$$\frac{V_1 - V_s}{R_s} + \frac{V_1}{R_{TC}} + \frac{V_1 - V_2}{R_{CW}} = 0 \qquad \text{Eq. (1)}$$

Node 2:

$$\frac{V_2 - V_1}{R_{CW}} + \frac{V_2}{R_{LP}} + \frac{V_2 - V_3}{R_{LS}} = 0 \qquad \text{Eq. (2)}$$

Node 3:

$$\frac{V_3 - V_2}{R_{LS}} + \frac{V_3}{R_H} + \frac{V_3 - V_M}{R_M} = 0 \qquad \text{Eq. (3)}$$

Equation 1 can be rewritten as:

$$V_1 \left( \frac{1}{R_s} + \frac{1}{R_{TC}} + \frac{1}{R_{CW}} \right) = \frac{V_s}{R_s} + \frac{V_2}{R_{CW}} \qquad \text{Eq. (4A)}$$

Solving for $V_1$ yields:

$$V_1 = \frac{V_s}{R_s \Omega_1} + \frac{V_2}{R_{CW} \Omega_1} \qquad \text{Eq. (4B)}$$

where:

$$\Omega_1 = \frac{1}{R_s} + \frac{1}{R_{TC}} + \frac{1}{R_{CW}}$$

Equation 2 can be rewritten as:

$$V_2\left(\frac{1}{R_{CW}} + \frac{1}{R_{LP}} + \frac{1}{R_{LS}}\right) = \frac{V_1}{R_{CW}} + \frac{V_3}{R_{LS}} \quad \text{Eq. (4C)}$$

Then, substituting Equation (4B) for $V_1$ and solving for $V_2$ yields:

$$V_2 = \frac{V_S}{R_S R_{CW} \Omega_1 \Omega_2 \Omega_{22}} + \frac{V_3}{R_{LS} \Omega_2 \Omega_{22}} \quad \text{Eq. (5)}$$

where:

$$\Omega_2 = \frac{1}{R_{LS}} + \frac{1}{R_{LP}} + \frac{1}{R_{CW}};$$

and $$\Omega_{22} = 1 - \frac{1}{R_{CW}^2 \Omega_1 \Omega_2}$$

Equation 3 can be rewritten as:

$$V_3\left(\frac{1}{R_{LS}} + \frac{1}{R_H} + \frac{1}{R_M}\right) = \frac{V_2}{R_{LS}} + \frac{V_M}{R_M} \quad \text{Eq. (6)}$$

Solving for $V_3$ yields:

$$V_3 = \frac{V_2}{R_{LS}\Omega_3} + \frac{V_M}{R_M \Omega_3} \quad \text{Eq. (7)}$$

where:

$$\Omega_3 = \frac{1}{R_{LS}} + \frac{1}{R_H} + \frac{1}{R_M}$$

Then, substituting Equation (5) for $V_2$ and again solving for $V_3$ yields:

$$V_3 = \frac{V_S}{R_S R_{CW} R_{LS} \Omega_1 \Omega_2 \Omega_{22} \Omega_3 \Omega_{33}} + \frac{V_M}{R_M \Omega_3 \Omega_{33}} \quad \text{Eq. (8)}$$

where:

$$\Omega_{33} = 1 - \frac{1}{R_{LS}^2 \Omega_2 \Omega_{22} \Omega_3} \quad \text{Eq. (9)}$$

From Equation (8), we define $\Omega_M$ as follows:

$$\Omega_M = R_M \Omega_3 \Omega_{33} = R_M \Omega_3\left(1 - \frac{1}{R_{LS}^2 \Omega_2 \Omega_{22} \Omega_3}\right) \quad \text{Eq. (10)}$$

From Equation (8), we also define $\Omega_S$ as follows:

$$\Omega_S = R_S R_{CW} R_{LS} \Omega_1 \Omega_2 \Omega_3 \Omega_{22} \Omega_{33} \quad \text{Eq. (11)}$$

Substituting in for $\Omega_{22}$ and $\Omega_{33}$, yields:

$$\Omega_S = R_S R_{CW} R_{LS} \Omega_1 \Omega_2\left(1 - \frac{1}{R_{CW}^2 \Omega_1 \Omega_2}\right)\Omega_3\left(1 - \frac{1}{R_{LS}^2 \Omega_2 \Omega_{22} \Omega_3}\right) \quad \text{Eq. (12)}$$

and, multiplying terms yields:

$$\Omega_S = R_S R_{CW} R_{LS}\left(\Omega_1 \Omega_2 - \frac{1}{R_{CW}^2}\right)\left(\Omega_3 - \frac{1}{R_{LS}^2\left(\Omega_2 - \frac{1}{R_{CW}^2 \Omega_1}\right)}\right) \quad \text{Eq. (13)}$$

such that $V_3$ is defined as follows:

$$V_3 = \frac{V_S}{\Omega_S} + \frac{V_M}{\Omega_M} \quad \text{Eq. (14)}$$

$V_3$ is the general transchest transfer function for transthoracic cell response model 10 of FIG. 3, and applies equally as well to the alternative transthoracic cell response models 10 of FIGS. 4A and 4B. Equation 14 encapsulates the transchest elements and their association between a forcing function, $V_S$ (which models a defibrillation circuit and a shock pulse) and a myocardial cell membrane voltage, $V_M$.

With the general transchest transfer function determined, the design equations for a monophasic waveform (or the first waveform of a biphasic waveform) $\Phi_1$ may be determined. The design equations describe: (1) a cell's response transchest transfer function; (2) the optimal pulse duration of $\Phi_1$, and (3) the optimal capacitor for delivering $\Phi_1$. (It should be noted that means other than a capacitor or capacitor/inductor combinations may be used to deliver discharge shock pulses without departing from the spirit or scope of the invention; the transchest transfer function must be determined accordingly).

In developing the $\Phi_1$ design equations, forcing function $V_S$ is preferably replaced with a more specific description of the defibrillation circuitry that implements the shock pulse. In the present invention, the shock pulse is preferably a decaying exponential waveform that is represented by:

$$V_S = V_1 e^{\frac{-t}{\tau_1}} \quad \text{Eq. (15)}$$

where $V_1$ is the leading-edge voltage for the shock pulse, i.e., the initial $C_1$ capacitor voltage, and $\tau_1 R C_1$, where $R = R_S + R_B \cdot R_S$ represents the resistance of the defibrillation system including the electrodes and $R_B$ represents the body impedance, e.g., thoracic cage, chest wall, lungs (series, parallel), and heart, see Equation 29.

Next, with reference to FIG. 4, nodal analysis provides an equation for $V_M$:

$$C_M \frac{dV_M}{dt} + \frac{V_M - V_3}{R_M} = 0 \quad \text{Eq. (16)}$$

Rearranging Equation 16, yields:

$$C_M \frac{dV_M}{dt} + \frac{V_M}{R_M} = \frac{V_3}{R_M} \quad \text{Eq. (17)}$$

Next, substituting equation 14 as an expression for $V_3$ into Equation 17, the cell membrane response may be calculated as follows:

$$C_M \frac{dV_M}{dt} + \frac{V_M}{R_M} = \frac{1}{R_M}\left(\frac{V_S}{\Omega_S} + \frac{V_M}{\Omega_M}\right) \quad \text{Eq. (18)}$$

Moving all $V_M$ elements to the left side of the equation, yields:

$$C_M \frac{dV_M}{dt} + \frac{V_M}{R_M} - \frac{V_M}{R_M \Omega_M} = \frac{V_S}{R_M \Omega_S} \quad \text{Eq. (19)}$$

Moving the common multiplier $V_M/R_M$, yields:

$$C_M \frac{dV_M}{dt} + \frac{V_M}{R_M}\left(1 - \frac{1}{\Omega_M}\right) = \frac{V_S}{R_M \Omega_S} \quad \text{Eq. (20)}$$

Then, dividing through by $C_M$ and setting $\tau_M = R_M C_M$, yields:

$$\frac{dV_M}{dt} + \frac{V_M}{\tau_M}\left(1 - \frac{1}{\Omega_M}\right) = \frac{V_S}{\tau_M}\left(\frac{1}{\Omega_S}\right) \quad \text{Eq. (21)}$$

Equation 21 is now in the form of a general ordinary differential equation (ODE) that models the effects of any forcing function $V_S$ that represents a phase of a shock pulse waveform applied across the chest. More specifically, ODE Equation 21 models the effects of a general shock pulse phase $V_S$ on the myocardium, allowing one to determine cardiac cell response to the shock pulse phase.

Using the forcing function, a.k.a., the shock pulse phase, $V_S$, as defined by Equation 15, and substituting it into Equation 21, yields an ODE as indicated by Equation 22, that specifically models the phase of a capacitor discharged shock pulse waveform:

$$\frac{dV_M}{dt} + \frac{V_M}{\tau_M}\left(1 - \frac{1}{\Omega_M}\right) = \frac{V_1 e^{\frac{-t}{\tau_1}}}{\tau_M \Omega_S} \quad \text{Eq. (22)}$$

In Equation 22, $\tau_M = R_M C_M$ and represents the time constant of the myocardial cell in transthoracic cell response model 10. Further, $\tau_1 = R_S C_1$ and represents the time constant of $\Phi_1$, remembering that $R_S$ represents the resistance of the defibrillation system including the electrodes.

Equation 22, as a standard ODE equation, has the generic form of:

$$\frac{dy}{dx} + P(x)Y = Q(x) \quad \text{Eq. (23)}$$

The generic solution to Equation 23 is as follows:

$$Y = e^{-\int Pdx}\left[\int e^{\int Pdx} Q dx + c\right] \quad \text{Eq. (24)}$$

As such, solving equation 22 using the method of integration factors, yields:

$$V_{M1}(t) = k e^{-\left(\frac{t}{\tau_M}\right)\left(1 - \frac{1}{\Omega_M}\right)} + \left(\frac{V_1}{\Omega_S}\right)\left(\frac{\tau_1}{\tau_1\left(1 - \frac{1}{\Omega_M}\right) - \tau_M}\right) e^{\frac{-t}{\tau_1}} \quad \text{Eq. (25)}$$

Equation 25 is an expression of myocardial cell membrane potential during $\Phi_1$ of a shock pulse. To determine the constant of integration, k, the initial value of $V_{M1}$ is assumed to be equal to cell ground, i.e., $V_{M1}(0) = V_G$. Applying this initial condition to Equation 25, k is defined as follows:

$$k = V_G - \left(\frac{V_1}{\Omega_S}\right)\left(\frac{\tau_1}{\tau_1\left(1 - \frac{1}{\Omega_M}\right) - \tau_M}\right) \quad \text{Eq. (26)}$$

Next, it is assumed, as indicated above, that $\tau_1 = RC_1$, where $R = R_S + R_B$. Again, $R_S$ represents the resistance of the defibrillation system including the electrodes and $R_B$ represents the body impedance, e.g., thoracic cage, chest wall, lungs (series, parallel), and heart. Note that to determine body impedance, $R_B$, from FIG. 3, the series and parallel combination of resistances must be addressed. As such, the series combination of $R_H$ and $R_{LS}$ yields $R_H + R_{LS}$. The parallel combination of $R_H + R_{LS}$ and $R_{LP}$ yields:

$$\frac{R_{LP}(R_{LS} + R_H)}{R_{LP} + R_{LS} + R_H} \quad \text{Eq. (27)}$$

The series combination of Equation 27 and $R_{CW}$ yields:

$$R_{CW} + \frac{R_{LP}(R_{LS} + R_H)}{R_{LP} + R_{LS} + R_H} \quad \text{Eq. (28)}$$

Finally, the parallel combination of Equation 28 and $R_{TC}$ yields the result for $R_B$:

$$R_B = \left(\frac{R_{TC}\left(R_{CW} + \frac{R_{LP}(R_{LS} + R_H)}{(R_{LP} + R_{LS} + R_H)}\right)}{R_{TC} + R_{CW} + \frac{R_{LP}(R_{LS} + R_H)}{(R_{LP} + R_{LS} + R_H)}}\right) \quad \text{Eq. (29)}$$

Knowing the value for $\tau_1$, as indicated above, the solution to the initial value problem for $\Phi_1$ is:

$$V_{M1}(t) = V_G e^{-\left(\frac{t}{\tau_M}\right)\left(1 - \frac{1}{\Omega_M}\right)} + \quad \text{Eq. (30)}$$

$$\left(\frac{V_1}{\Omega_S}\right)\left(\frac{\tau_1}{\tau_1\left(1 - \frac{1}{\Omega_M}\right) - \tau_M}\right)\left(e^{-\left(\frac{t}{\tau_M}\right)\left(1 - \frac{1}{\Omega_M}\right)}\right)$$

Equation 30 describes the residual voltage found on a cell at the end of $\Phi_1$.

Next, assuming $V_G = 0$ and $V_1 = 1$, the solution for cell response to an external shock pulse, i.e. design equation number 1 for $\Phi_1$, is:

$$V_{M1}(t) = \left(\frac{1}{\Omega_S}\right)\left(\frac{\tau_1}{\tau_1\left(1 - \frac{1}{\Omega_M}\right) - \tau_M}\right)\left(e^{\frac{-t}{\tau_M}} - e^{-\left(\frac{t}{\tau_M}\right)\left(1 - \frac{1}{\Omega_M}\right)}\right) \quad \text{Eq. (31)}$$

The optimal duration for $\Phi_1$ may now be determined according to criteria for a desired cell response. One such criterion is that the duration of $\Phi_1$ be equal to the time required for the external defibrillator shock pulse to bring the cell response to its maximum possible level. To determine this time duration, Equation 31 is differentiated and the resulting equation, Equation 32 is set equal to zero, i.e.,:

$$\left(\frac{AB}{\tau_M}\right)e^{\frac{-Bt}{\tau_M}} - \left(\frac{A}{\tau_1}\right)e^{\frac{-t}{\tau_1}} = 0 \quad \text{Eq. (32)}$$

Where $$A = \left(\frac{1}{\Omega_S}\right)\left(\frac{\tau_1}{\tau_1\left(1 - \frac{1}{\Omega_M}\right) - \tau_M}\right);$$

and $$B = 1 - \frac{1}{\Omega_M}$$

Then, solving for t, i.e., the optimal duration $d\Phi_1$, which represents the shock pulse duration required to maximize cardiac cell response for a monophasic shock pulse or $\Phi_1$ of a biphasic shock pulse, yields design equation 2 for $\Phi_1$:

$$d\Phi_1 = \left(\frac{\tau_1 \tau_M}{\tau_1\left(1 - \frac{1}{\Omega_M}\right) - \tau_M}\right)\ln\left(\frac{\tau_1\left(1 - \frac{1}{\Omega_M}\right)}{\tau_M}\right) \quad \text{Eq. (33)}$$

With the design equations for $\Phi_1$ determined, the design equations for $\Phi_2$ (the second waveform of a biphasic waveform) may be similarly determined. These design equations describe: (1) the myocardial cell membrane response to the transchest transfer function when plied with a second forcing function $V_S$; (2) the optimal pulse duration of $\Phi_2$; and (3) the optimal capacitor for delivering $\Phi_2$.

For $\Phi_2$, an analysis almost identical to Equations 22 through 33 above is derived. However, there are two identifiable differences. First, a biphasic waveform reverses the flow of current through the myocardium during $\Phi_2$. Reversing the flow of current in transthoracic cell response model 10 (FIG. 3,) changes the sign of the current and, as such, the sign on the right hand side of equation 22 is changed to a negative. Second, the $C_2$ capacitor bank, rather than the $C_1$ capacitor bank, delivers the shock pulse for $\Phi_2$ and, as such, $C_2$ rather than $C_1$ is incorporated into the design equations. Correspondingly, the leading-edge voltage $V_2$ of $C_2$ is also incorporated into the design equations rather than leading-edge voltage $V_1$. Thus, with respect to $\Phi_2$, the first-order linear ODE may be defined as:

$$\frac{dV_M}{dt} + \frac{V_M}{\tau_M}\left(1 - \frac{1}{\Omega_M}\right) = \frac{-V_2 e^{\frac{-t}{\tau_2}}}{\tau_M \Omega_S} \quad \text{Eq. (34)}$$

where: $\tau_2 = RC_2$ and represents the $\Phi_2$ time constant; and $$\frac{-V_2 e^{\frac{-t}{\tau_2}}}{\tau_M \Omega_S} = V_S,$$

the $\Phi_2$ forcing function.

The general solution of Equation 34 is defined as follows:

$$V_{M2}(t) = ke^{-\left(\frac{t}{\tau_M}\right)\left(1 - \frac{1}{\Omega_M}\right)} - \left(\frac{V_2}{\Omega_S}\right)\left(\frac{\tau_2}{\tau_2\left(1 - \frac{1}{\Omega_M}\right) - \tau_M}\right) \quad \text{Eq. (35)}$$

To determine the constant of integration, k, the initial value of $V_{M2}$ is set equal to the voltage, $V_{\Phi 1}$, left on the myocardial cell membrane at the end of the overall discharge time, $d\Phi_1$, of $\Phi_1$, i.e.,:

$$V_{M2}(0) = V_{M1}(d\Phi_1) = V_{\Phi 1} \quad \text{Eq. (36)}$$

Applying the initial condition to Equation 35 and solving for k yields:

$$k = V_{\Phi I} - \left(\frac{V_2}{\Omega_S}\right)\left(\frac{\tau_2}{\tau_2\left(1 - \frac{1}{\Omega_M}\right) - \tau_M}\right) \quad \text{Eq. (37)}$$

Following therefrom, the solution for myocardial cell membrane response to the second phase $\Phi_2$ of a biphasic waveform, i.e., design equation 1 for $\Phi_2$, is as follows:

$$V_{M2}(t) = \left(\frac{V_2}{\Omega_S}\right)\left(\frac{\tau_2}{\tau_2\left(1 - \frac{1}{\Omega_M}\right) - \tau_M}\right)\left(e^{-\left(\frac{t}{\tau_M}\right)\left(1 - \frac{1}{\Omega_M}\right)} - e^{\frac{-t}{\tau_2}}\right) + \quad \text{Eq. (38)}$$

$$V_{\Phi I}\left(e^{-\left(\frac{t}{\tau_M}\right)\left(1 - \frac{1}{\Omega_M}\right)}\right)$$

As such, Equation 38 provides the means to calculate the residual membrane potential at the end of $\Phi_2$ for those myocardial membrane cells not stimulated by $\Phi_1$. Equation 38 is then preferably set equal to zero and solved for t to determine the optimal time duration for $\Phi_2$, designated $d\Phi_2$. By designing $\Phi_2$ with the optimal duration, $\Phi_2$ operates to remove the residual charge placed on the myocardial membrane cell by $\Phi_1$ and helps to prevent refibrillation. As such, the optimal time duration, i.e., design equation 2 for $\Phi_2$ is determined to be:

$$d\Phi_2 = \quad \text{Eq. (39)}$$

$$\left(\frac{\tau_2 \tau_M}{\tau_2\left(1 - \frac{1}{\Omega_M}\right) - \tau_M}\right)\ln\left(1 + \left(\frac{\tau_2\left(1 - \frac{1}{\Omega_M}\right) - \tau_M}{\tau_M}\right)\left(\frac{\Omega_S V_{\Phi I}}{V_2}\right)\right)$$

Thus, from the equations above, an optimal monophasic defibrillation waveform or a biphasic defibrillation waveform may be calculated for an external defibrillator. It should be noted that the design of $\Phi_2$ is substantially independent of $\Phi_1$. To design $\Phi_2$, the only information necessary from $\Phi_1$ is the residual voltage left on the myocardial cell membrane after delivery of the $\Phi_1$ shock wave pulse. Additionally, it should be noted that $\Phi_2$ need not use the same or similar circuitry as $\Phi_1$ to deliver its shock pulse waveform. For example, $\Phi_1$ may use the capacitive discharge circuit of FIG. 3, while $\Phi_2$ may use the capacitor-inductor discharge circuit of FIG. 4B, and vice-versa.

Moreover, while the above has made mention of monophasic/biphasic truncated and non-truncated (full-tilt) exponential waveforms for delivering pulse shocks, the design equations of transthoracic cell response model may be used for other types of waveforms. By way of example, reference is once again made to FIGS. 4A and 4B, which preferably deliver a damped sine wave waveform having a forcing function of the form:

$$V_S = V_1\left(\frac{\tau_{CI}}{\tau_{CI} - \tau_{LI}}\right)\left(e^{\frac{-t}{\tau_{CI}}} - e^{\frac{-t}{\tau_{LI}}}\right) \text{ for } \Phi_1 \quad \text{Eq. (40)}$$

where $V_1$ is the leading-edge voltage on the charging capacitor bank $C_1$, $\tau_{C1} = RC_1$, and $$\tau_{LI} = \frac{L_1}{R}; R = R_S + R_B$$

as described above. A similar forcing function applies for $\Phi_2$ of a biphasic waveform wherein $V_2$, $C_2$, and $L_2$ are used in place of $V_1$, $C_1$, and $L_1$.

Implementation of Full-Tilt Exponential Waveform Design

Figure 5:
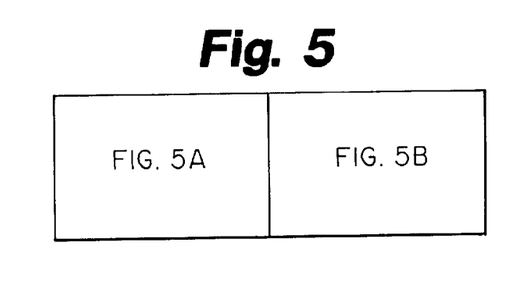
FIG. 5 depicts a block diagram of a pulse delivery circuit.
Figure 5A:
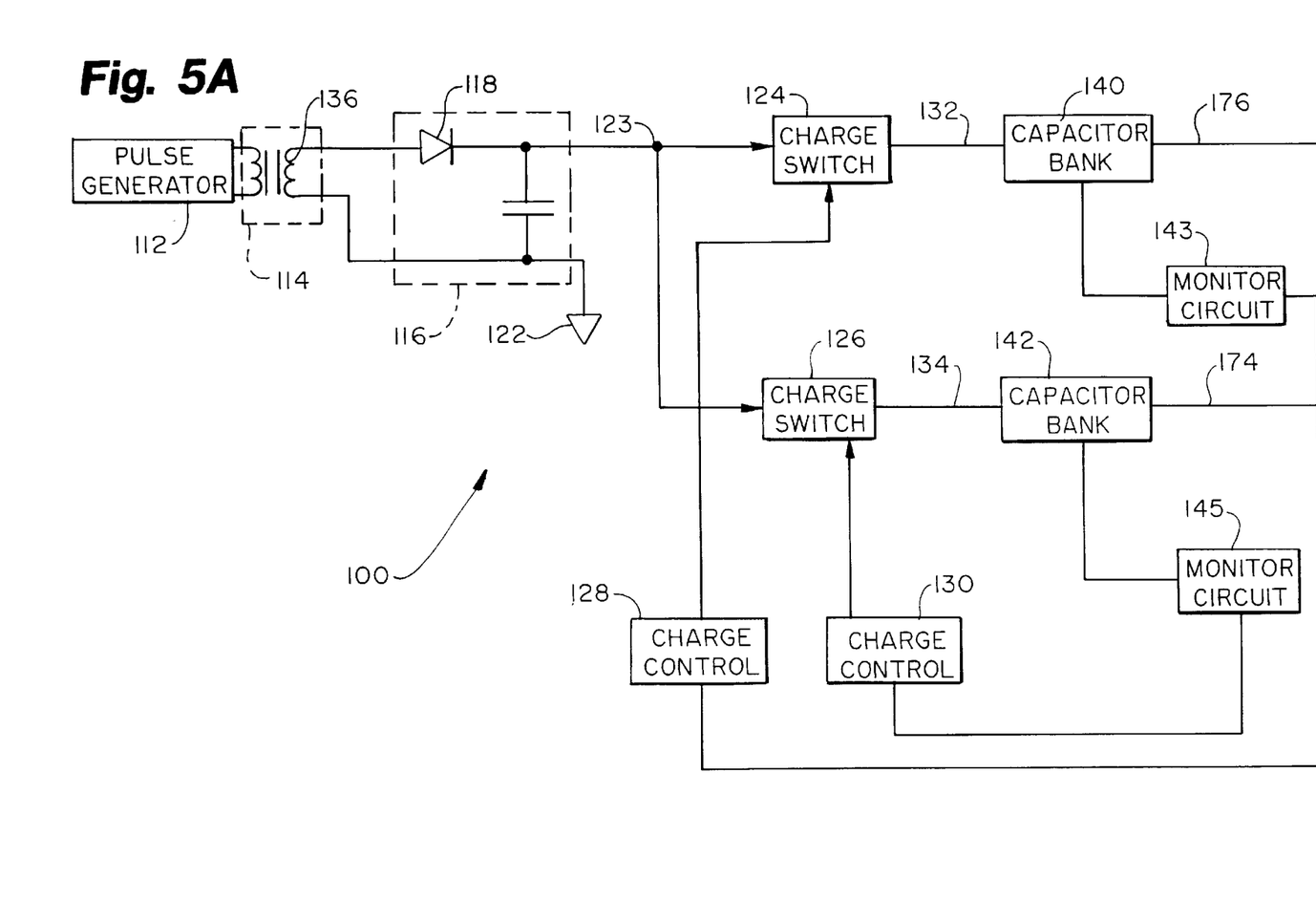
Figure 5B:
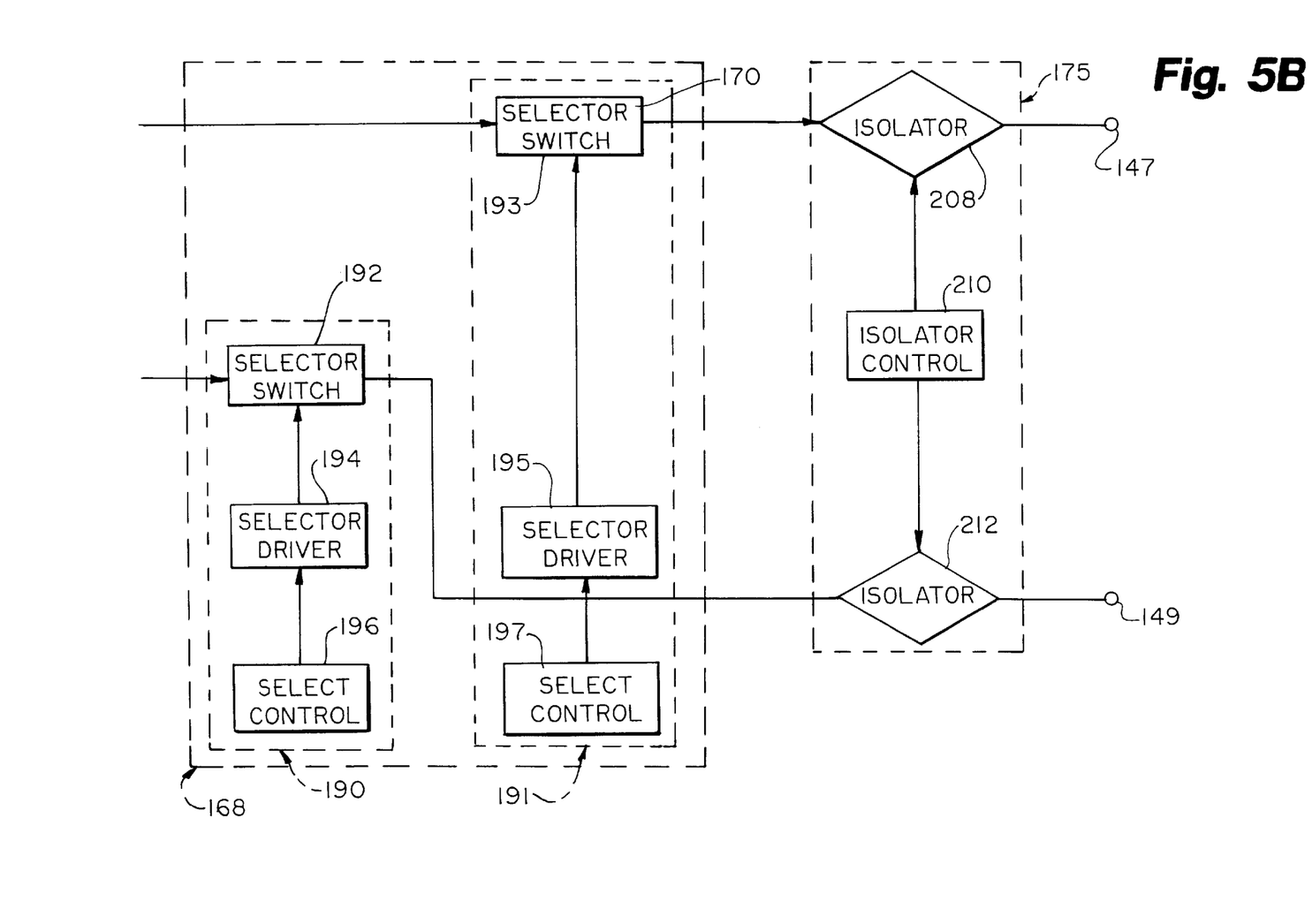

In the preferred embodiment of the present invention, the equations developed above are preferably used to design the characteristics of a full-tilt exponential waveform that may be used for monophasic and biphasic external defibrillation. Meanwhile, the design equations of the standard charge burping model may be used to design the characteristics of a full-tilt exponential waveform that may be used for monophasic and biphasic internal defibrillation. The waveform design characteristics are then preferably implemented within a pulse delivery circuit 100 as shown in FIG. 5.

Pulse delivery circuit 100, generally includes a pulse generator 112 connected to a pulse transformer 114 which, in turn, is connected to a passive rectifying and filtering circuit 116. Passive rectifying and filtering circuit 116 incorporates a diode 118 and capacitor 120, which is preferably in the 3–10 microFarad range. Circuit common is indicated by an inverted triangle 122, and an output 123 of circuit 116 is connected to first and second charge switches 124 and 126, respectively.

Charge switches 124 and 126 are each preferably formed of one or more solid state switching devices such as a silicon controlled rectifier (SCR), a field effect transistor (FET), an insulated gate bipolar transistor (IGBT) or other appropriate device. Such devices may be connected in series (to increase voltage capability) or in parallel (to increase current capability) as is known in the art.

Each charge switch 124 and 126 is preferably controlled by a separate charge control circuit 128 and 130, respectively. And, the respective outputs 132 and 134 of charge switches 124 and 126 are each individually connected to a capacitor bank; output 132 connected to capacitor bank 140 and output 134 connected to capacitor bank 142. Note that additional capacitor banks may be included without departing from the spirit or scope of the invention. Capacitor bank 140 is monitored by monitor circuit 143, which is connected between capacitor bank 140 and charge control circuit 128. Capacitor bank 142 is monitored by monitor circuit 145, which is connected between capacitor bank 142 and charge control circuit 130.

Figure 6:
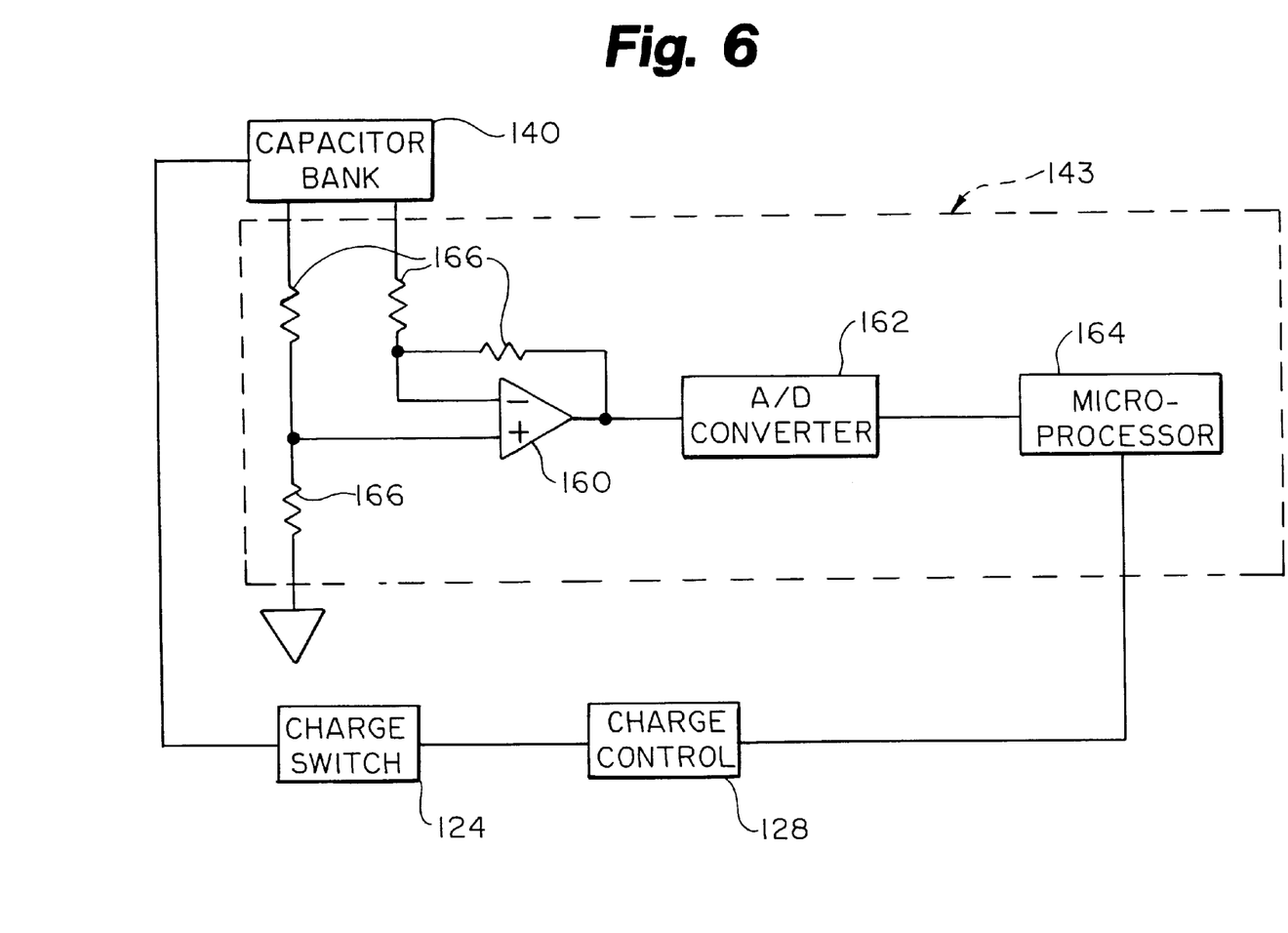
FIG. 6 depicts a block diagram of a voltage monitoring circuit that is incorporated with the pulse deliver circuit of FIG. 5.

One embodiment of voltage monitoring circuit 143 is illustrated in FIG. 6; voltage monitoring circuit 145 is the same as voltage monitoring circuit 143. Voltage monitoring circuit 143 generally includes an operational amplifier 160, an analog to digital converter 162 and a microprocessor 164. Amplifier 160 is connected to capacitor bank 140 via a plurality of resistors 166. In operation, voltage monitoring circuit 143 has a database of preset values stored in microprocessor 164. When capacitor bank 140 reaches a preset charging voltage value, as selected in microprocessor 164, charge control circuit 128 is instructed to halt the charging of capacitor bank 140. Of course, other types of voltage monitoring circuits may be used within pulse delivery circuit 100 without departing from the spirit or scope of the invention.

Pulse delivery circuit 100 further includes an output portion 168 that is connected to capacitor banks 140, 142. Output portion includes a selector circuit 170 and an isolator circuit 172 as indicated. Each capacitor bank 140, 142 has respective phase delivery command lines 174, 176, which carry notice from selector switch 170, 192 that either capacitor bank 140 or capacitor bank 142 is to release its energy.

Selector circuit 170 has a pair of preferably identical selector subsystems 190, 191. Subsystem 190 includes a solid state phase selector switch 192 connected to a phase selector driver 194 which in turn is connected to a select phase control 196, e.g., a microprocessor. Likewise, subsystem 191 includes a solid state phase selector switch 193 connected to a phase selector driver 195 which in turn is connected to a select phase control 197. Select phase controls 196, 197 provide signals to activate and deactivate their respective phase selector drivers 194, 195. Selector circuit 170 is preferably under microprocessor control, e.g., microprocessor 164, or, alternatively, may configured with other operable means such as hard wiring.

In explaining the operation of pulse delivery circuit 100 it is presumed, by way of example, that capacitor bank 140 is configured to discharge a positive first phase of a biphasic output pulse and that capacitor bank 142 is configured to discharge a negative second phase. As such, in operation pulse delivery circuit 100 is designed to output to electrode terminals 147 and 149 a high voltage defibrillation pulse, e.g., 2000–3000 volts. If pulse delivery circuit 100 is implemented within an external defibrillator, typical impedance values range between 25 and 225 ohms and, as such, currents in excess of 100 amps may be present. In order to generate and deliver the voltage levels desired for defibrillation, a two-step process is required.

The first step is that of charging the capacitors. Charge control circuits 128, 130 and charge switch circuits 124, 126 are used to charge capacitor banks 140, 142 to the desired voltage levels.

The second step is that of delivering the defibrillation pulse. In this step, pulse generator 112 supplies a series, or train, of wave pulses. By way of non-limiting example, a square wave pulse at 50% duty cycle having an amplitude of approximately 400 volts, at a frequency between approximately 5 KHz and 500 KHz, is an appropriate wave pulse. Generally, the wave pulses have very fast rapid rise times. Since the fast rise times and high frequencies of the pulses cause typically cause avalanching of most common solid state devices of reasonable cost, the pulses are first passed through passive filter circuit 116. Diode 118 is a fast recovery diode that provides for charging of capacitor 120 and prevents discharge of capacitor 120 through secondary 136 of pulse transformer 114.

In general, use of a pulse train with a very rapid rise time on individual pulses is desired, but would lead to avalanche breakdown of standard switches if coupled directly thereto. This would cause the switches to lose control of charging, and might lock the switches on thereby causing the capacitors to be continually charged until they are destroyed. The loss of charging control is undesirable and, thus, the use of rectifying and filtering circuit 116 avoids avalanche triggering of solid state switches 124, 126 allowing ordinary solid state devices to be used for switches 124, 126.

Now that the supplied pulse train has been rectified and filtered, step two, that is the delivery of the full-tilt exponential defibrillation pulse waveform, preferably proceeds under the following sequence:

(1) Phase selector switch 193 is turned ON, providing a first, positive polarity, exponentially decaying portion of the defibrillation pulse to the patient. To achieve this objective, phase selector driver 195 is activated to drive selector switch 193 to a state of conduction (ON) between lines 176 and 178, connecting capacitor bank 140 to isolator circuit 172 and ultimately to electrodes 147, 149 to deliver the first phase of the full-tilt exponential waveform defibrillation pulse.

(2) Phase selector switch 193 is turned OFF, when current flowing through phase selector switch 193 is nearly zero; the current is determined to be nearly zero when monitor circuit 143, by monitoring the voltage of capacitor bank 140, determines that the voltage on capacitor bank 140 is close to zero. To achieve this objective, select phase control 197 deactivates its phase selector driver 195 whereby phase selector switch 193 is rendered nonconductive (OFF), thus, stopping any remainder (of which there is little) of the first phase portion of the biphasic pulse from being delivered from capacitor bank 140.

(3) After a time delay, e.g., 0.5 milliseconds or the manufactured specified time to turn switch 193 off, phase selector switch 192 is turned ON, providing a second, negative polarity, exponentially decaying portion of the pulse. To achieve this objective phase selector driver 194 is activated to drive selector switch 192 to a state of conduction (ON) between lines 174 and 175, connecting capacitor bank 142 to isolator circuit 172 and ultimately, to electrodes 147, 149 to deliver the second phase of the full-tilt exponential waveform defibrillation pulse.

(4) Phase selector switch 192 is turned OFF, when current flowing through phase selector switch 192 is nearly zero; the current is determined to be nearly zero when monitor circuit 145, by monitoring the voltage of capacitor bank 142, determines that the voltage on capacitor bank 142 is close to zero. To achieve this objective, select phase control 196 deactivates its phase selector driver 194 whereby phase selector switch 192 is rendered nonconductive (OFF), thus, stopping any remainder (of which there is little) of the second phase portion of the biphasic pulse from being delivered from capacitor bank 142.

In view of the above sequence, it is evident that pulse delivery circuit 100 is essentially acting as a current controller in delivering a defibrillation.

Note that to provide a monophasic defibrillation pulse, only subsystem 191 is activated and steps (1) and (2) of the above-listed sequence are used.

Note that isolator circuit 172 is provided to keep the patient separate from the defibrillator and its defibrillation circuit 100. Without isolator circuit 172, leakage current from defibrillator circuit 100 might undesirably reach the patient and additional energy from the patient, such as that delivered by a second defibrillator, might reach defibrillation circuit 100 and alter its operation. More details regarding isolation circuits may be found in U.S. Pat. No. 5,909,138, which is hereby incorporated by reference.

Figure 7:
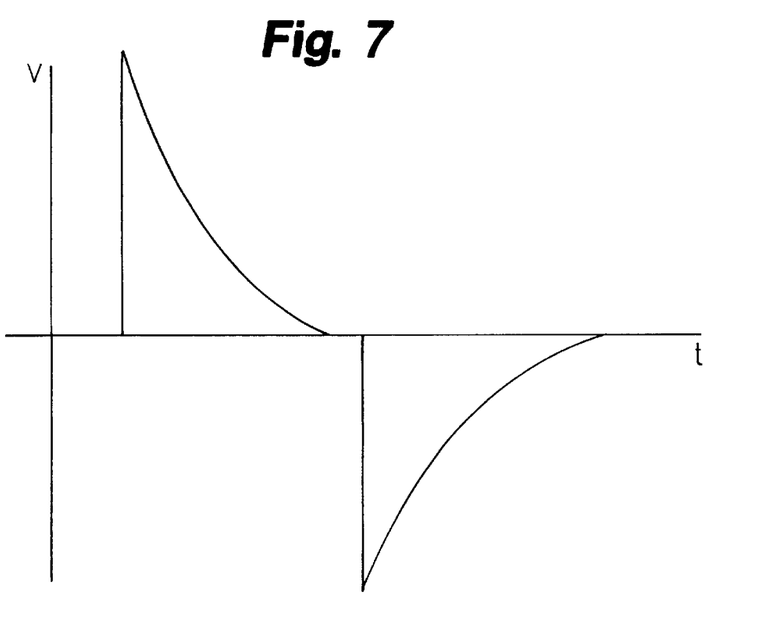
FIG. 7 depicts a biphasic full-tilt exponential waveform.

A biphasic full-tilt exponential waveform created by the steps above is shown in FIG. 7. A monophasic full-tilt exponential waveform comprises only the positive portion of FIG. 7.

It should be noted that in the above sequence, phase selector switches 192 and 193 are not actuated when they are conducting significant amounts of current. Turning phase selector switches 192 and 193 OFF when the current flowing through it is small (relative to the current used for defibrillation) results in less stress on phase selector switches 192 and 193 and, thereby, less likelihood of switch failure.

Figure 8:
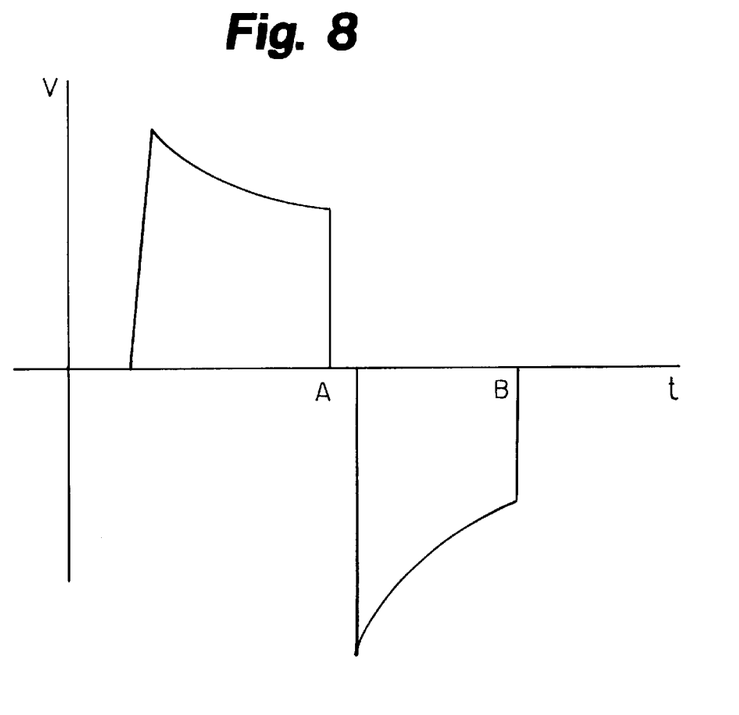
FIG. 8 depicts a prior art truncated exponential waveform.

In a standard truncated exponential waveform, as shown in FIG. 8, phase selector switch 193 would be turned OFF at time A and phase selector switch 192 would be turned OFF at time B thereby truncating the exponentially decaying pulse. This truncation occurs during the delivery of the pulse when there is still high current and high voltage flowing through the phase selector switch mechanisms causing great wear on the mechanism. As such, great care must be taken to the design of switching mechanisms to assure that they may be switched off while a high voltage current is flowing through them. This great care is not required of the full-tilt exponential waveform and, as such, cheaper components may be used. Alternatively, the switches may be eliminated since truncation is essentially not required of the waveform.

Implementation of the Pulse Delivery Circuit

Pulse delivery circuit 100 is preferably implemented in an internal defibrillator, of which there are many available types, or in an external defibrillator.

Figure 9A:
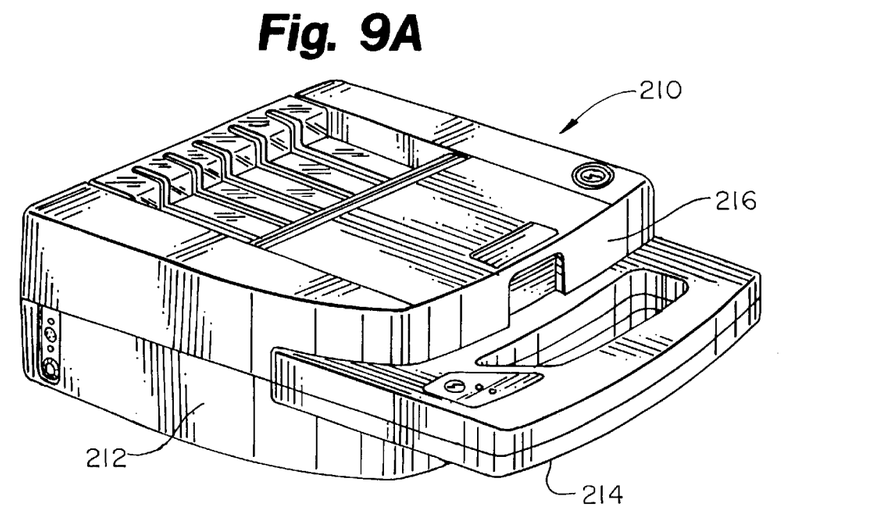
FIG. 9A depicts an automatic external defibrillator with a closed lid.
Figure 9B:
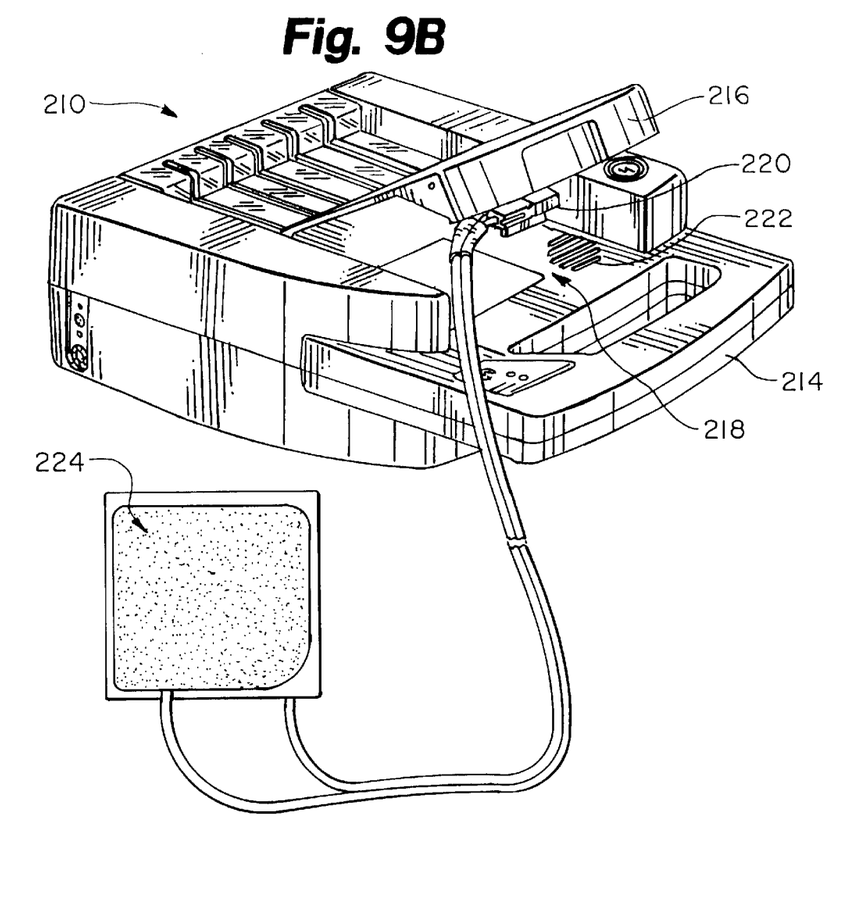
FIG. 9B depicts an automatic external defibrillator with an open lid.

One embodiment of an automated external defibrillator (AED) 210 is shown in FIGS. 9A and 9B. AED 210 includes a plastic case 212 with a carrying handle 214. A lid 216 is provided which covers an electrode compartment 218. An electrode connector 220, a speaker 222, and a diagnostic panel (not shown) are located on case 212 within electrode compartment 218. A pair of electrodes 147, 149 may be stored within compartment 218 and may be pre-connected to connector 220. The operation of AED 210 is described briefly below. A rescue mode of AED 210 is initiated when lid 216 is opened to access electrodes 224. The opening of lid 216 is detected by AED 210 to effectively turn on the device. AED 210 then quickly runs a short test routine. After electrodes 147, 149 have been placed on the patient, AED 210 senses patient specific parameters such as impedance, voltage, current, charge, or other measurable parameters of the patient. Any or all of these patient specific parameters may be utilized to design optimal, full-tilt exponential pulse delivery waveforms as described in the sections above.

If a shockable condition is detected through electrodes 147, 149 pulse delivery circuit 100, located within AED 210, operates to charge capacitor banks 140, 142 from an energy source, typically a detachable battery pack. Based upon the patient specific parameters sensed, the duration and other characteristics of the full-tilt exponential discharge waveform (monophasic or biphasic) are then calculated per the design equations described above. A microprocessor preferably performs the calculations. Then, using pulse delivery circuit 100 and the energy stored in capacitor banks 140, 142, the full-tilt exponential waveform is discharged to the patient through electrodes 147, 149.

For a more detailed description of the physical structure of AED 210 or the process involved in sensing, charging, shocking and testing, reference should be made to U.S. Pat. No. 5,645,571, entitled AUTOMATED EXTERNAL DEFIBRILLATOR WITH LID-ACTIVATED SELF-TEST SYSTEM; U.S. Pat. No. 5,645,571 is hereby incorporated by reference.

While the above has detailed in basic terms the operation of a certain internal defibrillator and a certain external defibrillator, it should be noted that numerous other internal and external defibrillators may be employed without departing from the spirit or scope of the invention.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention.

What is claimed:

1. A defibrillator comprising:

an energy source;

a capacitor system operably coupled to said energy source via a charging system;

the charging system being adapted for storing electrical energy in said capacitor system;

a monitoring circuit for monitoring the voltage on said capacitor system;

a selector switch circuit coupled to said monitoring circuit;

a processor and control logic circuit; and an electrode operably coupled to said capacitor system via said selector switch circuit wherein said capacitor system delivers an electrical pulse from said electrical energy stored in said capacitor system to said electrode in a full-tilt exponential defibrillation waveform controlled by the processor and control logic circuit, wherein said full-tilt exponential defibrillation waveform is truncated by the switching of said selector switch circuit at about ninety five percent of the full waveform of said electrical pulse at the same time a current flowing through said selector switch circuit is approximately zero amps wherein said zero amps is indicated by said monitoring circuit when said monitored voltage on said capacitor system is approximately zero, and wherein said full-tilt exponential waveform has delivered about ninety nine and seventy five one hundredths percent of the electrical energy of said electrical pulse at the time of truncation.

2. The defibrillator of claim 1, wherein said defibrillator is selected from a group consisting of an internal defibrillator and an external defibrillator.

3. The defibrillator of claim 1, wherein said electrical pulse is of the type of pulse selected from a group consisting of monophasic and biphasic pulse.

4. The defibrillator of claim 1, further comprising a sensor system wherein a characteristic of said electrical pulse is determined by said sensor system.

5. A defibrillator comprising:

means for providing energy;

means for storing energy operably coupled to said means for providing energy;

means for processing and controlling the providing, storing and delivery of energy;

means for monitoring the voltage of said stored energy;

means for switching coupled to said means for monitoring; and means for delivering an electrical pulse operably coupled, via said means for switching, to said means for storing energy, wherein said means for storing energy is also for releasing the stored-energy as said electrical pulse to said means for delivering in a full-tilt exponential defibrillation waveform wherein said full-tilt exponential defibrillation waveform is truncated by said means for switching at about ninety five percent of the full waveform of said electrical pulse at the same time a current flowing through said means for switching is approximately zero amps wherein said zero amps indicating that is indicated by the means for monitoring when said monitored voltage on said means for storing energy is approximately zero, and wherein said full-tilt exponential waveform has delivered about ninety nine and seventy five one hundredths percent of the electrical energy of said electrical pulse at the time of truncation.

6. The defibrillator of claim 5, wherein said defibrillator is selected from a group consisting of an internal defibrillator and an external defibrillator.

7. The defibrillator of claim 5, wherein said electrical pulse is of the type of pulse selected from a group consisting of a monophasic and a biphasic pulse.

8. The defibrillator of claim 5, further comprising a sensor system wherein a characteristic of said electrical pulse is determined by said sensor system.

9. A method of delivering a defibrillation pulse, comprising the steps of:

generating electrical energy;

storing said electrical energy; releasing at least a first portion of said stored electrical energy via a selector switch circuit in a pulse having a positive polarity exponentially decaying defibrillation waveform; monitoring the voltage of the stored electrical energy and stopping the release of said stored electrical energy upon a current in said selector switch reaching substantially zero amps when said monitored voltage of said stored electrical energy is approximately zero, resulting in said full-tilt exponential defibrillation waveform being truncated at about ninety five percent of the full waveform of said electrical pulse and in said full-tilt exponential defibrillation waveform delivering about ninety nine and seventy five one hundredths percent of the electrical energy of said electrical pulse at the time of truncation.

10. The method of claim 9, wherein said pulse is selected from a group consisting of a monophasic pulse and a first phase of a biphasic pulse.

11. The method of claim 9, further comprising the steps of releasing at least a second portion of said stored electrical energy in a pulse having a negative polarity exponentially decaying waveform and stopping the release of said electrical energy upon a current component of said electrical energy reaching substantially zero amps.

12. The method of claim 9, wherein said pulse is delivered by a defibrillator selected from a group consisting of an internal defibrillator and an external defibrillator.

* * * * *